(12) United States Patent
Tsuji et al.

(10) Patent No.: US 6,251,589 B1
(45) Date of Patent: *Jun. 26, 2001

(54) METHOD FOR DIAGNOSING SPINOCEREBELLAR ATAXIA TYPE 2 AND PRIMERS THEREFOR

(75) Inventors: Shoji Tsuji; Kazuhiro Sanpei, both of Niigata (JP)

(73) Assignee: SRL, Inc., Tachikawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/043,303
(22) PCT Filed: Jul. 18, 1996
(86) PCT No.: PCT/JP96/01999
  § 371 Date: May 18, 1998
  § 102(e) Date: May 18, 1998
(87) PCT Pub. No.: WO98/03679
  PCT Pub. Date: Jan. 29, 1998

(51) Int. Cl.[7] .................................................. C12Q 1/68
(52) U.S. Cl. ..................... 435/6; 435/91.1; 435/91.2; 536/23.1; 536/24.33; 536/24.3
(58) Field of Search ........................ 435/6, 91.1, 91.2; 536/23.1, 24.33, 24.3

(56) References Cited

U.S. PATENT DOCUMENTS 5,853,995 * 12/1998 Lee ........................................... 435/6

OTHER PUBLICATIONS

Pulst, "Anticipation in spinocerebellar ataxia type 2", Sep. 1993, Nature Genetics, vol. 5, pp. 8–10.*

Filla et al., "Has spinocerebellar ataxia type 2 a distinct phenotype?", Apr. 1995, Neurology, 45, pp. 793–796.*

Gispert et al., "Chromosomal assignment of the second locus for autosomal dominant cerebellar ataixa (SCA2) to chromosome 12q23–24.1", Jul. 1993, Nature Genetics, vol. 4, pp. 295–299.*

Yamagata et al., Jpn. J. Electroph., vol. 38(6), abstract, 1994.*

B. T. Teh et al., Am. J. Hum. Genet., vol. 56, pp. 1443–1449 (1995).

Y. Trottier et al., Nature, vol. 378, pp. 403–406 (1995).

Koide et al., Nature Genetics, vol. 6, pp. 9–13, (Jan. 1994).

Sanpei et al., Biochemical and Biophysical Research Communications, vol. 212, No. 2, pp. 341–346, (Jul. 1995).

* cited by examiner

Primary Examiner—Lisa B. Arthur
Assistant Examiner—Jeanine Goldberg
(74) Attorney, Agent, or Firm—Birch, Stewart, Kolasch & Birch, LLP

(57) ABSTRACT

A method for specifically diagnosing spinocerebellar ataxia type 2 (SCA2) is disclosed. In the method of the present invention, PCR is carried out using a first primer which hybridizes with a part of the nucleotide sequence shown in SEQ ID NO:1, a second primer which hybridizes with a part of the nucleotide sequence shown in SEQ ID NO:3, and a test DNA as a template, and the number of CAG repeats is measured in the amplified PCR product. Since the numbers of CAG repeat in the genes of SCA2 patients are not less than 35 while those of normal individuals are 15 to 24, diagnosis of SCA2 can be carried out by the method of the present invention.

8 Claims, 4 Drawing Sheets

FIG.1 gggaccgtatccctccgccgccccteccccgcccggccccggccccccteecteccggCAGAGCTCGCCCT
CCCTCCGCCTCAGACTGTTTTGGTAGCAACGGCAACGGCGGCGGCGCGTTTCGGCCCCGGCTCCCGGCGGC
TCCTTGGTCTCGGCGGGCCTCCCCGCCCCTTCGTCGTCGTCCTTCTCCCCCTCGCCAGCCCGGGCGCCCC
                                                C
TCCGGCCGCGCCAACCCGCGCCTCCCCGCTCGGCGCCCGTGCGTCCCCGCCGCGTTCCGGCCGTCTCCTTG
GCGCGCCCGGCTCCCGGCTGTCCCCGCCCGGCGTGCGAGCCGGTGTATGGGCCCCTCACCATGTCGCTGA
AGCCC (CAG)$_n$ (CCG CCG CAG) CCGCCGCCCGCGGCTGCCAATGTCCGCAAGCCCGGCGGCAGCGG
CCTTCTAGCGTCGCCCGCCGCCGCGCCTTCGCCGTCCTCGTCCTCGGTCTCCTCGTCCTCGGCCACGGCT
CCCTCCTCGGTGGTCGCGGCGACCTCCGGCGGCGGGAGCCCCGGCCTGGGCAGgtgggtgtcggcacccc
agccccccteegctccgggcc

FIG.2

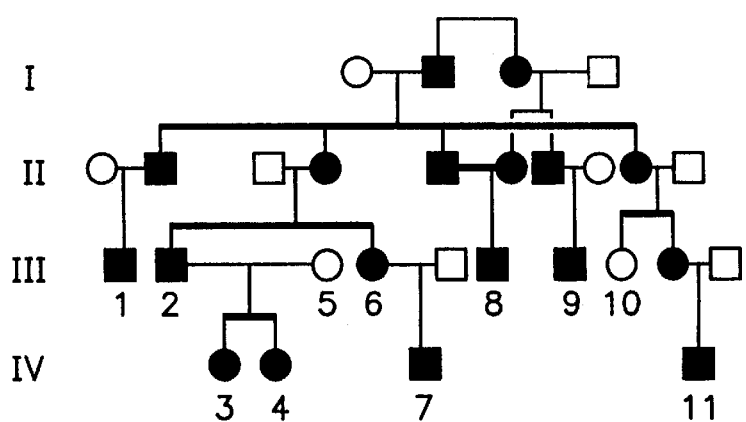

FIG. 3

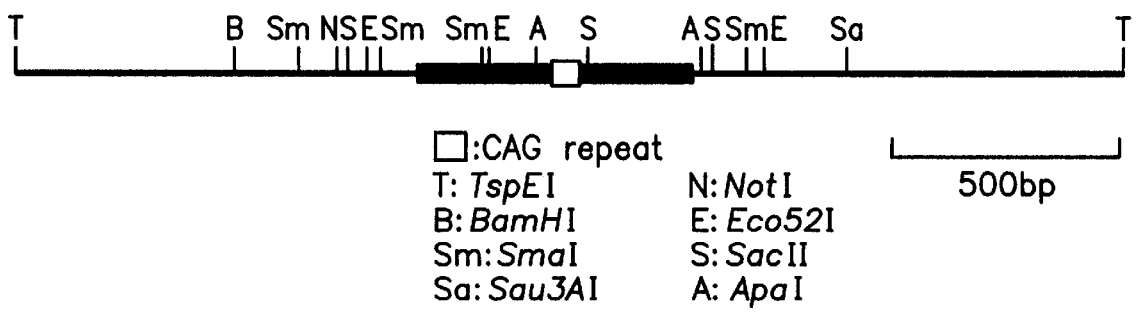

☐ : CAG repeat
T: TspEI    N: NotI
B: BamHI    E: Eco52I
Sm: SmaI    S: SacII
Sa: Sau3AI  A: ApaI 500bp

FIG. 4

```
  1 gggaccgtatccctccgccgcccctcccccgcccggccccggccccccctccctcccgg CA

61 GAGCTCGCCTCCCTCCGCCTCAGACTGTTTTGGTAGCAACGGCAACGGCGGCGGCGCGTT
                                                               C
121 TCGGCCCGGCTCCCGGCGGCTCCTTGGTCTCGGCGGGCCTCCCCGCCCCTTCGTCGTCGT

181 CCTTCTCCCCCTCGCCAGCCCGGGCGCCCCTCCGGCCGCGCCAACCCGCGCCTCCCCGCT
        C
241 CGGCGCCCGTGCGTCCCCGCCGCGTTCCGGCGTCTCCTTGGCGCGCCCCGGCTCCCGGCTG

301 TCCCCGCCCGGCGTGCGAGCCGGTGTATGGGCCCCTCACCATGTCGCTGAAGCCCCAGCA
                              F-1
                                         MetSerLeuLysProGlnGln

361 GCAGCAGCAGCAGCAGCAGCAACAGCAGCAGCAGCAACAGCAGCAGCAGCAGCAGCAGCC
    GlnGlnGlnGlnGlnGlnGlnGlnGlnGlnGlnGlnGlnGlnGlnGlnGlnGlnGlnPro

421 GCCGCCCGCGGCTGCCAATGTCCGCAAGCCCGGCGGCAGCGGCCTTCTAGCGTCGCCCGC
               R-2                         R-1
    ProProAlaAlaAlaAsnValArgLysProGlyGlySerGlyLeuLeuAlaSerProAla

481 CGCCGCGCCTTCGCCGTCCTCGTCCTCGGTCTCCTCGTCCTCGGCCACGGCTCCCTCCTC
    AlaAlaProSerProSerSerSerValSerSerSerSerAlaThrAlaProSerSer

541 GGTGGTCGCGGCGACCTCCGGCGGCGGGAGGCCCGGCCTGGGCAG gtgggtgtcggcacc
    ValValAlaAlaThrSerGlyGlyGlyArgProGlyLeuGly 601 ccagccccctccgctccgggcc
```

FIG.5

Normal chromosomes

5'-(CAG) 8 CAA(CAG) 4 CAA(CAG) 7 CCG CCG CCC GCG-3'

5'-(CAG) 8 CAA(CAG) 4 CAA(CAG) 8 CCG CCG CCC GCG-3'

5'-(CAG) 13 CAA(CAG) 8 CCG CCG CCC GCG-3'

5'-(CAG) 13 CAA(CAG) 5 CCG CCG CCC GCG-3'

5'-(CAG) 6 CAA(CAG) 8 CCG CCG CCC GCG-3'

SCA2 chromosomes

5'-(CAG) n CCG CCG CCC GCG-3'

5'-(CAG) n CCG CCG CAG CCG CCG CCC GCG-3' ional Application No. PCT/JP96/01999

SEQUENCE LISTING

<160> NUMBER OF SEQ ID NOS: 21

<210> SEQ ID NO 1
<211> LENGTH: 355
<212> TYPE: DNA
<213> ORGANISM: Homo sapiens
<220> FEATURE:
<221> NAME/KEY: CDS
<222> LOCATION: (341)..(355)

<400> SEQUENCE: 1

```
gggaccgtat ccctccgccg cccctccccc gcccggcccc ggccccctc cctccggca      60 gagctcgcct ccctccgcct cagactgttt tggtagcaac ggcaacggcg gcggcgcgtt    120
tcggcccggc tcccggcggc tccttggtct cggcgggcct ccccgcccct cgtcgtcgy    180 ccttctcccc ctcgccagcc cgggcgcccc tccggccgcg ccaacccgcg cctccccgct    240
cggcgcccgy gcgtccccgc cgcgttccgg cgtctccttg gcgcgccggg ctcccggctg    300
tccccgcccg gcgtgcgagc cggtgtatgg gcccctcacc atg tcg ctg aag ccc     355
                                              Met Ser Leu Lys Pro
                                                1               5
```

<210> SEQ ID NO 2
<211> LENGTH: 5
<212> TYPE: PRT
<213> ORGANISM: Homo sapiens

<400> SEQUENCE: 2

Met Ser Leu Lys Pro
  1               5

<210> SEQ ID NO 3
<211> LENGTH: 205
<212> TYPE: DNA
<213> ORGANISM: Homo sapiens
<220> FEATURE:
<221> NAME/KEY: CDS
<222> LOCATION: (1)..(174)

<400> SEQUENCE: 3

```
ccg ccg ccc gcg gct gcc aat gtc cgc aag ccc ggc ggc agc ggc ctt      48
Pro Pro Pro Ala Ala Ala Asn Val Arg Lys Pro Gly Gly Ser Gly Leu
  1               5                  10                  15 cta gcg tcg ccc gcc gcc gcg cct tcg ccg tcc tcg tcc tcg gtc tcc      96
Leu Ala Ser Pro Ala Ala Ala Pro Ser Pro Ser Ser Ser Ser Val Ser
             20                  25                  30 tcg tcc tcg gcc acg gct ccc tcc tcg gtg gtc gcg gcg acc tcc ggc     144
Ser Ser Ser Ala Thr Ala Pro Ser Ser Val Val Ala Ala Thr Ser Gly
         35                  40                  45 ggc ggg agg ccc ggc ctg ggc agg tgg gtg tcggcacccc agccccctc        194
Gly Gly Arg Pro Gly Leu Gly Arg Trp Val
     50                  55 cgctccgggc c                                                         205
```

<210> SEQ ID NO 4
<211> LENGTH: 58
<212> TYPE: PRT
<213> ORGANISM: Homo sapiens

<400> SEQUENCE: 4

Pro Pro Pro Ala Ala Ala Asn Val Arg Lys Pro Gly Gly Ser Gly Leu
  1               5                  10                  15

```
Leu Ala Ser Pro Ala Ala Ala Pro Ser Pro Ser Ser Ser Val Ser
             20                  25                  30

Ser Ser Ser Ala Thr Ala Pro Ser Val Val Ala Ala Thr Ser Gly
         35                  40                  45

Gly Gly Arg Pro Gly Leu Gly Arg Trp Val
         50                  55

<210> SEQ ID NO 5
<211> LENGTH: 623
<212> TYPE: DNA
<213> ORGANISM: Homo sapiens
<220> FEATURE:
<221> NAME/KEY: CDS
<222> LOCATION: (341)..(583)
<223> OTHER INFORMATION: Tsp-2

<400> SEQUENCE: 5
gggaccgtat ccctccgccg ccctccccc gcccggcccc ggccccctc cctccggca      60 gagctcgcct ccctccgcct cagactgttt tggtagcaac ggcaacgcg gcggcgcgtt    120 tcggcccggc tcccggcggc tccttggtct cggcgggcct ccccgcccct tcgtcgtcgy   180
ccttctcccc ctcgccagcc cgggcgcccc tccggccgcg ccaacccgcg cctccccgct   240
cggcgcccgy gcgtccccgc gcgttccgg cgtctccttg gcgcgcccgg ctcccggctg    300
tccccgcccg gcgtgcgagc cggtgtatgg gcccctcacc atg tcg ctg aag ccc    355
                                              Met Ser Leu Lys Pro
                                                1               5 cag cag cag cag cag cag cag cag caa cag cag cag cag caa cag cag    403
Gln Gln Gln Gln Gln Gln Gln Gln Gln Gln Gln Gln Gln Gln Gln Gln
                 10                  15                  20 cag cag cag cag cag ccg ccg ccc gcg gct gcc aat gtc cgc aag ccc    451
Gln Gln Gln Gln Gln Pro Pro Pro Ala Ala Ala Asn Val Arg Lys Pro
             25                  30                  35 ggc ggc agc ggc ctt cta gcg tcg ccc gcc gcc gcg cct tcg ccg tcc    499
Gly Gly Ser Gly Leu Leu Ala Ser Pro Ala Ala Ala Pro Ser Pro Ser
         40                  45                  50 tcg tcc tcg gtc tcc tcg tcc tcg gcc acg gct ccc tcc tcg gtg gtc    547
Ser Ser Ser Val Ser Ser Ser Ser Ala Thr Ala Pro Ser Ser Val Val
     55                  60                  65 gcg gcg acc tcc ggc ggc ggg agg ccc ggc ctg ggc aggtgggtgt         593
Ala Ala Thr Ser Gly Gly Gly Arg Pro Gly Leu Gly
 70                  75                  80 cggcacccca gcccccctcc gctccgggcc                                   623

<210> SEQ ID NO 6
<211> LENGTH: 81
<212> TYPE: PRT
<213> ORGANISM: Homo sapiens

<400> SEQUENCE: 6

Met Ser Leu Lys Pro Gln Gln Gln Gln Gln Gln Gln Gln Gln Gln
  1               5                  10                  15

Gln Gln Gln Gln Gln Gln Gln Gln Gln Gln Pro Pro Pro Ala Ala Ala
                 20                  25                  30

Asn Val Arg Lys Pro Gly Gly Ser Gly Leu Leu Ala Ser Pro Ala Ala
             35                  40                  45

Ala Pro Ser Pro Ser Ser Ser Ser Val Ser Ser Ser Ser Ala Thr Ala
         50                  55                  60
```

```
Pro Ser Ser Val Val Ala Ala Thr Ser Gly Gly Gly Arg Pro Gly Leu
 65                  70                  75                  80

Gly

<210> SEQ ID NO 7
<211> LENGTH: 203
<212> TYPE: DNA
<213> ORGANISM: p-2093 plasmid

<400> SEQUENCE: 7
caccaccagc aacagcaaca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcatcacg gaaactctgg gcc                                             203

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
caccaccagc aacagcaaca                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ggcccagagt ttccgtgatg                                                  20

<210> SEQ ID NO 10
<211> LENGTH: 75
<212> TYPE: DNA
<213> ORGANISM: Homo sapiens

<400> SEQUENCE: 10
cagcagcagc agcagcagca gcagcaacag cagcagcagc aacagcagca gcagcagcag      60
cagccgccgc ccgcg                                                       75

<210> SEQ ID NO 11
<211> LENGTH: 78
<212> TYPE: DNA
<213> ORGANISM: Homo sapiens

<400> SEQUENCE: 11
cagcagcagc agcagcagca gcagcaacag cagcagcagc aacagcagca gcagcagcag      60
cagcagccgc cgcccgcg                                                    78

<210> SEQ ID NO 12
<211> LENGTH: 78
<212> TYPE: DNA
<213> ORGANISM: Homo sapiens

<400> SEQUENCE: 12
```

-continued cagcagcagc agcagcagca gcagcagcag cagcagcagc aacagcagca gcagcagcag    60
cagcagccgc cgcccgcg                                                  78

<210> SEQ ID NO 13
<211> LENGTH: 69
<212> TYPE: DNA
<213> ORGANISM: Homo sapiens

<400> SEQUENCE: 13
cagcagcagc agcagcagca gcagcagcag cagcagcagc aacagcagca gcagcagccg    60
ccgcccgcg                                                            69

<210> SEQ ID NO 14
<211> LENGTH: 57
<212> TYPE: DNA
<213> ORGANISM: Homo sapiens

<400> SEQUENCE: 14
cagcagcagc agcagcagca acagcagcag cagcagcagc agcagccgcc gcccgcg       57

<210> SEQ ID NO 15
<211> LENGTH: 15
<212> TYPE: DNA
<213> ORGANISM: Homo sapiens

<400> SEQUENCE: 15
cagccgccgc ccgcg                                                     15

<210> SEQ ID NO 16
<211> LENGTH: 24
<212> TYPE: DNA
<213> ORGANISM: Homo sapiens

<400> SEQUENCE: 16
cagccgccgc agccgccgcc cgcg                                           24

<210> SEQ ID NO 17
<211> LENGTH: 165
<212> TYPE: DNA
<213> ORGANISM: Artificial Sequence
<220> FEATURE:
<223> OTHER INFORMATION: Description of Artificial Sequence:Probe

<400> SEQUENCE: 17
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcag                   165

<210> SEQ ID NO 18
<211> LENGTH: 572
<212> TYPE: DNA
<213> ORGANISM: Homo sapiens
<220> FEATURE:
<221> NAME/KEY: variation
<222> LOCATION: (356)..(358)
<223> OTHER INFORMATION: The CAG repeat unit formed by nucleotides
      356-358 varies in the number of repeats present.
<221> NAME/KEY: variation
<222> LOCATION: (359)..(367)
<223> OTHER INFORMATION: Nucleotides 359-367 may be either present of
      absent.

<400> SEQUENCE: 18

```
-continued gggaccgtat ccctccgccg cccctccccc gcccggcccc ggccccccctc cctcccggca      60 gagctcgcct ccctccgcct cagactgttt tggtagcaac ggcaacggcg gcggcgcgtt     120
tcggcccggc tcccggcggc tccttggtct cggcgggcct ccccgcccct tcgtcgtcgy     180
ccttctcccc ctcgccagcc cgggcgcccc tccggccgcg ccaacccgcg cctccccgct     240
cggcgcccgy gcgtccccgc cgcgttccgg cgtctccttg gcgcgccgg ctcccggctg      300 tccccgcccg gcgtgcgagc cggtgtatgg gcccctcacc atgtcgctga agccccagcc    360
gccgcagccg ccgcccgcgg ctgccaatgt ccgcaagccc ggcggcagcg gccttctagc     420
gtcgcccgcc gccgcgcctt cgccgtcctc gtcctcggtc tcctcgtcct cggccacggc    480
tccctcctcg gtggtcgcgg cgacctccgg cggcgggagg cccggcctgg gcaggtgggt    540
gtcggcaccc cagcccccct ccgctccggg cc                                   572

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer F-1

<400> SEQUENCE: 19
tcaccatgtc gctgaagccc                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer R-1

<400> SEQUENCE: 20
gggcgacgct agaaggccgc                                                   20

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Primer R-2

<400> SEQUENCE: 21
gcggacattg gcagc                                                        15
```

METHOD FOR DIAGNOSING SPINOCEREBELLAR ATAXIA TYPE 2 AND PRIMERS THEREFOR This application claims the benefit under 35 U.S.C. §371 of prior PCT International Application No. PCT/JP96/01999 which has an International filing date of Jul. 18, 1996 which designated the United States of America, the entire contents of which are hereby incorporated by reference.

TECHNICAL FIELD

The present invention relates to a method for diagnosing spinocerebellar ataxia type 2 (hereinafter also referred to as "SCA2") and primers therefor.

BACKGROUND ART

SCA2 is an autosomal dominant, neurodegenerative disorder that affects the cerebellum and other areas of the central nervous system.

It has recently been discovered that the causative genes of five neurodegenerative diseases including dentatorubral-pallidoluysian atrophy (DRPLA) have more CAG repeats than the normal genes. That is, the numbers of CAG repeats in the causative genes of the neurodegenerative diseases are 37 to 100, while those in the normal genes are less than 35.

It has been suggested that the causative gene of SCA2 has an increased number of CAG repeats (Trottier, Y. et al. Nature, 378, 403–406 (1995)). However, since the causative gene of SCA2 has not been identified, and since its nucleotide sequence has not been determined, SCA2 cannot be diagnosed by a genetic assay.

DISCLOSURE OF THE INVENTION

Accordingly, an object of the present invention is to provide a method for diagnosing SCA2 by genetic assay and to provide primers therefor.

The present invention intensively studied to discover after carrying out Southern blot analysis using a $^{32}$P-labeled single-stranded DNA probe containing 55 CAG repeats (this probe is hereinafter also referred to as "(CAG)$_{55}$ probe" (SEQ ID NO:17) on the genomic DNA fragments obtained by digesting the genomic DNAs of SCA2 patients and normal individuals, that a TspEI fragment with a size of 2.5 kb is detected only in SCA2 patients. The (CAG)$_{55}$ probe selectively partially hybridizes with a DNA region having not less than about 35 CAG repeats by appropriately selecting the hybridization conditions. The 2.5 kb TspEI fragment was cloned and sequenced. On the other hand, by carrying out Southern blot analysis on the genomic DNAs of normal individuals using the cloned DNA fragment as a probe, normal genes were obtained and sequenced. Comparison between the genes from the SCA2 patients and the genes from the normal individuals revealed that the numbers of the CAG repeats were different and the other portions were substantially the same. Primers were selected such that the CAG repeats are interposed therebetween and PCR was carried out. By measuring the size of the PCR product, the number of CAG repeats in the PCR product was determined. The number of the CAG repeats was measured for 34 chromosomes from SCA2 patients and 286 chromosomes from normal individuals. As a result, in all of the SCA2 genes, the numbers of the CAG repeats were not less than 35, while in normal genes, there were 15 to 24. Therefore, by measuring the number of CAG repeats, the genetic diagnosis of SCA2 can be attained.

That is, the present invention provides a method for diagnosing spinocerebellar ataxia type 2, comprising carrying out PCR using a first primer which hybridizes with a part of the nucleotide sequence shown in SEQ ID NO:1, a second primer which hybridizes with a part of the nucleotide sequence shown in SEQ ID NO:3, and a test DNA as a template, and measuring the number of CAG repeats in the amplified PCR product. The present invention also provides the above-mentioned first and second primers which are used for the above-described method.

By the present invention, genetic diagnosis of SCA2 was first accomplished. Therefore, it is expected that the present invention will greatly contribute to the diagnosis of SCA2.

BRIEF DESCRIPTION OF THE DRAWINGS

FIG. 1 shows the nucleotide sequence (SEQ ID NO:18) of the causative gene of SCA2;

FIG. 2 is a pedigree chart of the SCA2 patients who donated the genomic DNAs used in the Examples;

FIG. 3 is a restriction map of Tsp-2 which is a genomic DNA fragment originated from a normal allele;

FIG. 4 shows the nucleotide sequence [SEQ ID NO:5 (DNA) and SEQ ID NO:6 (amino acid)] of Tsp-2 together with the regions with which each primer hybridizes;

FIG. 5 shows nucleotide sequences (SEQ ID NO:10–16, from top to bottom) of the region of the CAG repeats and of the region immediately thereafter;

BEST MODE FOR CARRYING OUT THE INVENTION

Figure 6:
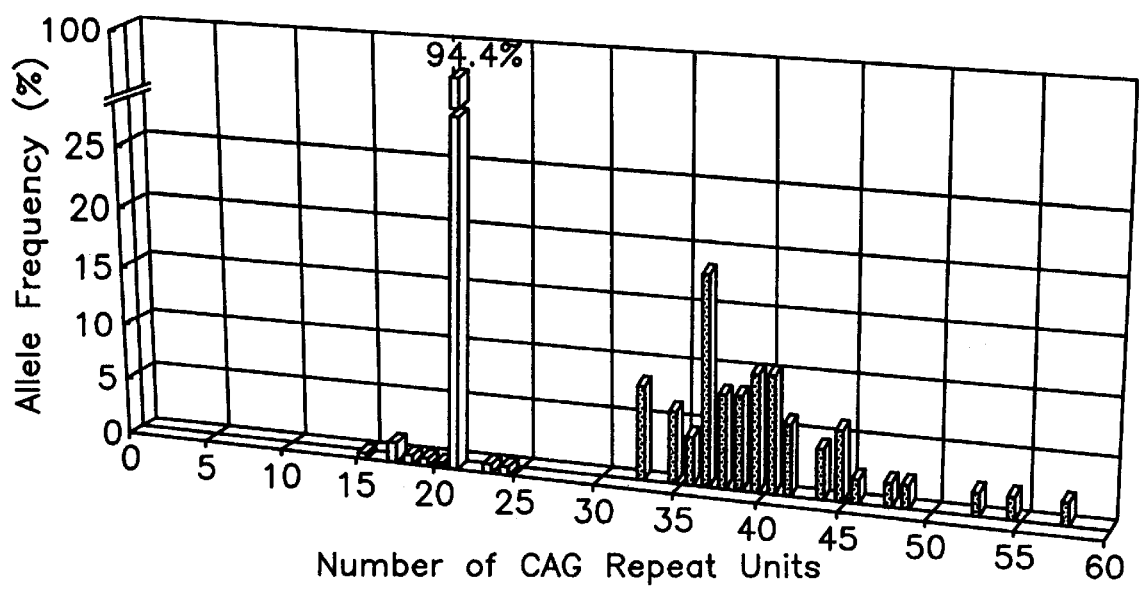
FIG. 6 shows the distribution of the numbers of the CAG repeat units in the normal and SCA2 genes, which were measured by the method according to the present invention.

As will be described in detail in the Examples below, the partial nucleotide sequences of the causative genes of SCA2 were determined by the present invention, and the partial nucleotide sequences of the corresponding genes of normal individuals were also determined. Comparison between the SCA2 causative genes and the normal genes revealed that the numbers of CAG triplet repeats in the genes are different. More particularly, as will be described in detail in the Examples below, the SCA2 genes have 35 to 55 CAG repeat units while in normal individuals, the numbers of the CAG repeats were 15 to 24, and 94.4% of the normal individuals had 22 CAG repeats. Thus, it was proved that SCA2 can be diagnosed by measuring the number of the CAG repeat units.

The nucleotide sequence of the gene participating in the onset of SCA2, which was determined by the present invention, is shown in FIG. 1. In FIG. 1, the region indicated by (CAG)$_n$ is the region of the CAG triplet repeats. The region of (CCG CCG CAG) may or may not be contained in the SCA2 gene, and is not contained in the normal gene. The region shown in uppercase letters is the region of which sequence was determined form both genomic DNA and cDNA, and the regions shown in lowercase letters are the regions of which sequences were determined in the genomic DNA and the cDNA are shown in two layers and the upper character indicate the base determined from the cDNA.

As will be described in detail in the Examples below, although there are some other minor differences, the main difference between the SCA2 gene and the normal gene resides in the number of CAG repeat units shown as $(CAG)_n$ in FIG. 1. Thus, by measuring the number of the CAG repeat units, SCA2 can be diagnosed.

In the method of the present invention, to measure the number of the CAG repeat units, the region including the CAG repeat region is amplified by PCR. This can be accomplished by carrying out the PCR using primers hybridizing with the regions upstream and downstream of the CAG repeat region, respectively.

The nucleotide sequence of the region upstream of the CAG repeat region is shown in SEQ ID NO:1 in the SEQUENCE LISTING, and that of the region downstream of the CAG repeat region is shown in SEQ ID NO:3. PCR is performed using oligonucleotide primers which hybridize with the sense chain and the antisense chain of the regions in the upstream and downstream regions of the CAG repeat region, respectively. Any primers which hybridize with any part of the above-mentioned regions may be employed. The size of the primer is not restricted and usually 15 to 50 nucleotides, preferably 18 to 25 nucleotides.

Using these primers, and using a test DNA as the template, PCR is performed. The test DNA is the DNA sampled from a person to be diagnosed for SCA2, and may be prepared from peripheral blood or the like by a conventional method. In cases where the primers which hybridize with the regions upstream and downstream of the CAG repeat regions, respectively, which regions are shown in uppercase letters in FIG. 1, are employed, not only genomic DNA, but also cDNA may be used as the template. Since the PCR method per se is well-known in the art and a kit therefor is commercially available, PCR can be easily carried out. The details of the PCR are also described in the Examples below.

Then the number of the CAG repeat units in the amplified PCR product is measured. This may be carried out by, for example, sequencing the PCR product. Alternatively, this may be carried out by performing gel electrophoresis together with appropriate markers and determining the size of the PCR product. In the Examples described below, gel electrophoresis using SCA2 genes having slightly varying numbers of CAG repeat units as size markers was carried out so as to determine the size of the PCR product and, in turn, the number of the CAG repeat units contained therein. It should be noted that the methods for measuring the number of the CAG repeat units in the PCR product are not restricted to the above-mentioned methods, and any method which can determine the number of the CAG repeat units may be employed. Further, a method which can only distinguish whether the number of CAG repeat units is about not less than 35 or not may also be employed. Such a method is also included in the method for "measuring the number of the CAG repeat units" in the context of the present invention. For example, a probe such as a $(CAG)_{55}$ probe mentioned above may be subjected to hybridization with the PCR product in a condition under which it hybridizes only with the DNAs having not less than about 35 CAG repeat units.

EXAMPLES

The present invention will now be described in more concretely by way of examples. It should be understood, however, the examples are presented for the illustration purpose only and should not be interpreted in any restrictive way.

Reference Example 1 Preparation of $(CAG)_{55}$ Probe

A genomic DNA segment of DRPLA gene containing a CAG repeat with 55 repeat units was amplified from the genomic DNA of a patient with DRPLA (Koide, R. et al., Nature Genet., 6, 9–13 (1994)) and was subcloned into a plasmid vector, pT7Blue T (p-2093). The p-2093 plasmid contains the $(CAG)_{55}$ and the flanking sequences. That is, the plasmid contains the sequence of 5'-CAC CAC CAG CAA CAG CAA $(CAG)_{55}$ CAT CAC GGA AAC TCT GGG CC-3' (SEQ ID NO:7). Using a pair of oligonucleotides 5'-CAC CAC CAG CAA CAG CAA CA-3' SEQ ID NO:8 and 5'-biotin-GGC CCA GAG TTT CCG TGA TG-3' (SEQ ID NO:9), PCR was performed in a total volume of 16 μl containing 10 mM Tris-HCl, pH8.3, 50 mM KCl, 1.5 mM $MgCl_2$, 2M N,N,N-trimethylglycine, 0.1 mM TTP, 0.1 Mm dCTP, 0.1 mM dGTP, 9.25 MBq of $[\alpha\text{-}^{32}P]daT$ (222 TBq/mmol), 0.5 mM each of the two primers, 0.3 ng of plasmid DNA (p-2093) and 2.0 U of Taq DNA polymerase (Takara Shuzo, Kyoto, Japan). After an initial 2-min. denaturation at 94° C., PCR was performed for 30 cycles consisting of 1-min. denaturation at 94° C., 1-min. annealing at 54° C. and 3-min. extension at 72° C., followed by a final extension at 72° C. for 10 min.

A single-stranded $(CAG)_{55}$ probe was isolated using streptavidin-coated magnetic beads (Kynabeads M-280, Streptavidin; Dynal AS, Oslo, Norway). That is, after washing of the PCR products immobilized on the magnetic beads with 40 μl of a solution containing 5 mM Tris-HCl (pH 7.5), 0.5 mM EDTA and 1 M NaCl, the non-biotinylated strand containing the radio-label was separated from the biotinylated strand by incubation in 50 μl of 0.1 M NaOH for 10 min. The resultant supernatant was directly added to the hybridization solution described below.

Incidentally, using the single-stranded $(CAG)_{55}$ probe prepared as described above, Southern blot analysis was carried out on the androgen receptor genes containing 9, 22, 43 and 51 CAG repeat units, respectively. As a result, the $(CAG)_{55}$ probe strongly hybridized with the genes having 43 and 51 CAG repeats units, respectively, but scarcely hybridized with the gene having 22 CAG repeat units, and did not hybridize at all with the gene having 9 CAG repeat units (K. Sanpei et al., Biochemical and Biophysical Research Communications, Vol. 212, No.2, 1995, pp. 341–346). Thus, by using this probe, hybridization may be selectively attained only with DNAs containing a number of (e.g., 35 or more) CAG repeat units if the hybridization conditions are appropriately selected.

EXAMPLE 1 Determination of Nucleotide Sequence of SCA2 Gene

FIG. 2 shows a pedigree chart of SCA2 patients. In this pedigree chart, males are represented by squares and females are represented by circles. SCA2 patients are represented by black squares or circles, and unaffected persons are represented by white squares or circles.

High-molecular-weight genomic DNA (15 μg) was digested with 100 U of TspEI (Toyobo, Osaka, Japan), electrophoresed through 1.0% agarose gels and transferred to nitrocellulose membranes. The membranes were hybridized with the $(CAG)_{55}$ probe described above. Hybridization was performed in a solution containing 2.75×SSPE (1×SSPE=150 mM NaCl, 10 mM $NaH_2PO_4$, 1 mM EDTA), 50% formamide, 5×Denhardt's solution, 100 ng/ml of sheared salmon sperm DNA and the $(CAG)_{55}$ probe ($6 \times 10^6$ cpm/ml) at 62° C. for 18 hours. After the hybridization, the membranes were washed with 1×SSC (150 mM NaCl, 15 mM sodium citrate) containing 0.5% SDS at 65° C. for 0.5 hours. The membranes were autoradiographed for 16 hours to Kodak Bio Max MS film at −70° C. using an MS intensifying screen.

As a result, 2.5 kbp TspEI fragment hybridized with the probe was detected only in all of the SCA2 patients.

Genomic DNA (270 μg) from an SCA2 patient (individual 7 in FIG. 2) was digested by TspEI and subjected to agarose gel electrophoresis. Genomic DNA fragments including the 2.5 kb TspEI fragment were cloned into an EcoRI-cleaved λZAPII vector. The genomic library was screened using the $(CAG)_{55}$ probe under the hybridization condition described above. A genomic clone, Tsp-1; containing an expanded CAG repeat was isolated.

After removal of the probe, the above-described genomic library was screened again using the Tsp-1 as a probe, which was labeled by the random priming. Hybridization was carried out in a solution containing 5×SSC, 1×Denhardt's solution, 10% dextran sulfate, 20 mM sodium phosphate, 400 μg/ml human placental DNA and the Tsp-1 probe at 42° C. for 18 hours. After the hybridization, the membrane were washed finally in 0.1×SSC–0.1% SDS at 52° C. for 0.5 hours. The membranes were autoradiographed for 24 hours to Kodak Bio Max MS films at −70° C. using an MS intensifying screen. As a result, a genomic clone, Tsp-2, originated from a normal allele was isolated.

A restriction map of Tsp-2 is shown in FIG. 3. The CAG repeat (open box) is located in the putative first exon (solid box).

Nucleotide sequence of the SmaI-ApaI fragment (630 bp) of Tsp-2 was determined. The sequence is shown in FIG. 4 and in SEQ ID NO:5 in the SEQUENCE LISTING. In FIG. 4, the region of which sequence was determined from both the genomic DNA and cDNA (described below) is shown in uppercase letters and the regions of which sequences were determined from the cDNA is shown in lowercase letters. The sites at which the base is different in the genomic DNA and the cDNA are shown in two layers and the upper character indicate the base determined from the cDNA. The deduced amino acid sequence is shown below the nucleotide sequence. Translation initiated from the ATG codon in the longest open reading frame in the putative first exon.

A human cerebral cortex cDNA library (Clonetech, Palo Alto, Calif., USA) was screened using oligonucleotides, F-1 (SEQ ID NO:19) (SEQ ID NO:20), designed to flank the CAG repeat as shown in FIG. 4, as the probes. Hybridization was performed for 18 hours at 55° C. in a solution containing 6×SSC, 10×Denhardt's solution, 0.5% SDS, 0.05% sodium pyrophosphate, 100 ng/ml sheared salmon sperm DNA and the end-labeled oligonucleotide probe. After the hybridization, the membranes were washed finally in 6×SSC containing 0.5% SDS and 0.05% sodium pyrophosphate for 0.5 hours at 55° C. A clone, Fc-1, which gave a hybridization signal with both the oligonucleotide probes, was obtained. To identify the 5' end of the cDNA, 5'-RACE was performed using 5'-RACE-Ready cDNA (Clonetech, Palo Alto, Calif. USA). The primer R-1 was used in the primary PCR and the primer R-2 (SEQ ID NO:21) (see FIG. 4) was used in the secondary PCR. As the forward primer, F-1 (see FIG. 4) was used in both the primary and secondary PCR. The 5'-RACE product, 350 bp in size, was subcloned into a pT7Blue T vector (5'-RACE-1). The identity of 5'-RACE-1 was confirmed by the overlap of the nucleotide sequence with those of Fc-1, Tsp-1 and Tsp-2. Nucleotide sequences were determined by the dideoxynucleotide chain termination method using double-stranded plasmid DNAs as the templates.

PCR products obtained from genomic DNA of normal and SCA2-affected individuals using the primer pair of F-1 (forward side) and R-1 (reverse side) were cloned into a plasmid vector, pT7Blue, followed by determination of the nucleotide sequence. The results are shown in FIG. 5.

As shown in FIG. 5, the normal genes have one or two CAA, while SCA2 genes do not. Further, in SCA2 genes, CCG CCG CAG may be inserted into the site immediately after the CAG repeat region.

EXAMPLE 2 Measurement of CAG Repeat Units in Sample

Numbers of CAG repeat units were determined by polyacrylamide gel electrophoresis analysis of PCR products obtained using the primer pair of F-1 and R-1. PCR was performed in a total volume of 10 μl containing 10 mM Tris-HCl, pH 8.3, 50 mM KCl, 2.0 mM $MgCl_2$, 1.7 M N,N,N-trimethylglycine, 111KBq of [α-$^{32}$P] dCTP (111 Tbq/mmol), 30 μM dCTP, and 200 μM each of dATP, dGTP and TTP, 0.25 μM each of the two primers, 200 ng of genomic DNA and 1.25 U of Taq DNA polymerase. After an initial 2-min denaturation at 95° C., PCR was performed for 32 cycles of 1-min denaturation at 95° C., 1-min annealing at 60° C. and 1-min extension at 72° C., followed by a final extension at 72° C. for 5 min. Sequence ladders obtained using the cloned genomic segments of the SCA2 gene, which contain various sizes of CAG repeats, were used as size markers. For normal alleles containing one or two CAA interruptions, the numbers of the CAA units were included in the CAG repeat size. For SCA2 alleles having expanded CAG region, the above-mentioned insert sequence immediately after the CAG region was not included in the size of the CAG region.

By the above-described method, the numbers of the CAG repeat units of normal individuals (286 chromosomes) and 10 pedigrees of SCA2 patients (34 SCA2 chromosomes) were determined. The results are shown in FIG. 6. In FIG. 6, open bars indicate the results of the normal genes and solid bars indicate the results of the SCA2 genes.

As is apparent from FIG. 6, in all of the normal genes, the numbers of the CAG repeat units were not more than 24, while in all of the SCA2 genes, they were not less than 35. Thus, it was proved that genetic diagnosis of SCA2 can be attained by the method of the present invention.

Figure 7:
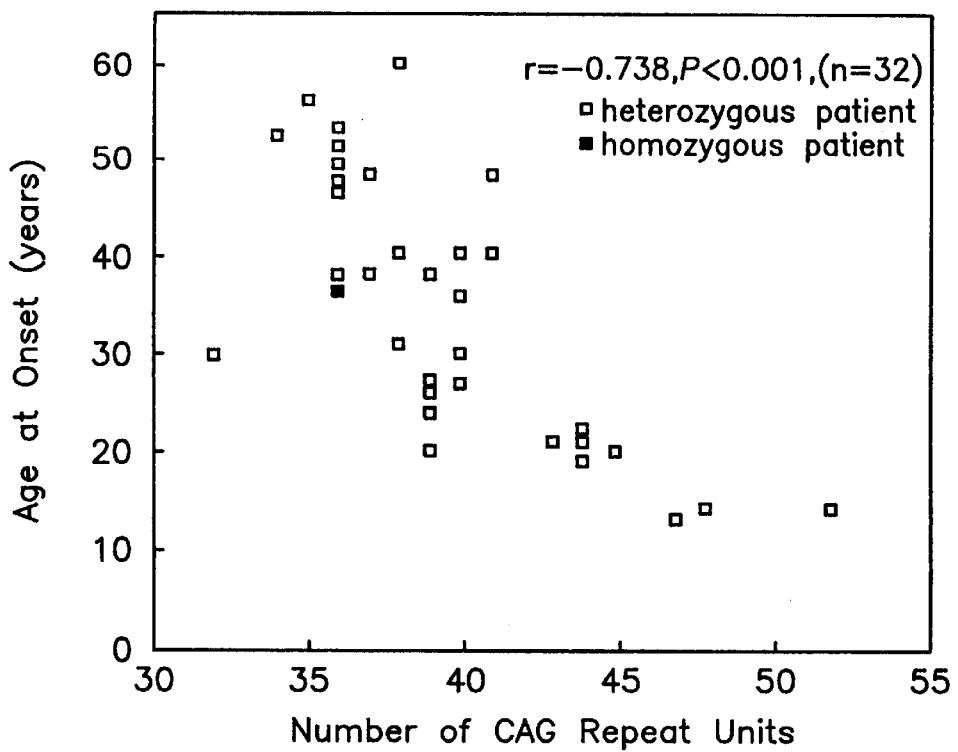
FIG. 7 shows the relationship between the number of CAG repeat units and the age of onset of SCA2.

The relationship between the number of the CAG repeat units determined by the method described above and the age at onset of symptoms of SCA2 is shown in FIG. 7. An inverse correlation was observed statistically. This suggests that expansion of the number of the CAG repeat units relates to the onset of symptoms of SCA2.

INDUSTRIAL AVAILABILITY

By the present invention, genetic assay of SCA2 was first attained. Thus, it is expected that the present invention will greatly contribute to the diagnosis of SCA2.

What is claimed is:

1. A method for diagnosing spinocerebellar ataxia type 2 in a human nucleic acid sample comprising the steps of:
    amplifying said nucleic acid sample with a first primer and a second primer by polymerase chain reaction, wherein said first primer hybridizes to a region of SEQ ID NO:1 and said second primer hybridizes to a region of SEQ ID NO:3;
    obtaining an amplification product of said nucleic acid sample by said polymerase chain reaction; and
    measuring a number of CAG repeats in said amplification product,
    wherein a number of 35 or more CAG repeats in said nucleic acid sample is indicative of said spinocerebellar ataxia type 2 and a number of 15–24 CAG repeats in said nucleic acid sample would be negative for spinocerebellar ataxia type 2.

2. The method of claim 1, wherein said first primer has a sequence as in SEQ ID NO:19.

3. The method of claim 1, wherein said second primer has a sequence as in SEQ ID NO:20.

4. The method of claim 1, wherein said number of CAG repeats is measured by gel electrophoresis.

5. The method of claim 1, wherein said number of CAG repeats is measured by sequencing said amplification product.

6. The method of claim 1, wherein said number of CAG repeats is measured by hybridizing a probe to said amplification product, wherein said probe has a sequence of SEQ ID NO:17.

7. The method of claim 1, wherein the nucleic acid sample is a genomic DNA.

8. The method of claim 1, wherein the nucleic acid sample is a cDNA.

* * * * *